US012685854B2

(12) United States Patent
    Ripanti

(10) Patent No.: US 12,685,854 B2
(45) Date of Patent: Jul. 21, 2026

(54) TATTOO MACHINE INK DISPENSER RESERVOIR STRUCTURE

(71) Applicant: Tiziano Ripanti, Ancona (IT)

(72) Inventor: Tiziano Ripanti, Ancona (IT)

( * ) Notice: Subject to any disclaimer, the term of this patent is extended or adjusted under 35 U.S.C. 154(b) by 543 days.

(21) Appl. No.: 18/276,966

(22) PCT Filed: Feb. 11, 2022

(86) PCT No.: PCT/EP2022/053377
    § 371 (c)(1),
    (2) Date: Aug. 11, 2023

(87) PCT Pub. No.: WO2022/175179
    PCT Pub. Date: Aug. 25, 2022

(65) Prior Publication Data
    US 2024/0115845 A1      Apr. 11, 2024

(30) Foreign Application Priority Data
    Feb. 18, 2021    (IT) ......................... 102021000003716

(51) Int. Cl.
    *A61M 37/00*          (2006.01)
(52) U.S. Cl.
    CPC .............................. *A61M 37/0084* (2013.01)
(58) Field of Classification Search
    CPC .............. A61M 37/00; A61M 37/0015; A61M
                37/0076; A61M 37/0084; A61M 39/22;
                A61M 39/24; A61M 2205/07; A61M
                2205/071; A61M 2205/121; A61M
    2205/123; A61M 2207/00; A61B 5/0532;

A61B 17/3401; A61B 17/3403; B26F
1/32; A01K 11/005; A61K 8/11; A61K
2800/43; Y10T 74/18056
See application file for complete search history.

(56) References Cited

U.S. PATENT DOCUMENTS

| | | | | |
|---|---|---|---|---|
| 4,286,599 A | * | 9/1981 | Hahn | ........................ A61D 7/00 |
| | | | | 606/116 |
| 2008/0033470 A1 | * | 2/2008 | Kluge | ............... A61M 37/0084 |
| | | | | 606/186 |
| 2016/0074646 A1 | | 3/2016 | Norman | |

FOREIGN PATENT DOCUMENTS

| | | | | |
|---|---|---|---|---|
| DE | 202014009857 | | 12/2015 | |
| EP | 0004669 B1 | * | 10/1980 | ........... A01K 11/005 |
| EP | 3517163 | | 7/2019 | |
| WO | WO-2017131337 A1 | * | 8/2017 | ........ A61M 37/0084 |

* cited by examiner

*Primary Examiner* — Robert J Scruggs
(74) *Attorney, Agent, or Firm* — Themis Law

(57) ABSTRACT

A tattoo machine ink dispenser reservoir structure includes a handle having at least two seats to house and retain at least two ink cartridges each provided with an occluding element pierced or adapted to be pierced for the introduction of air when in use; a skin needle connected to the handle; a connecting system that connects the at least two ink cartridges with the skin needle and that includes at least two nozzles; and a pneumatic pump, wherein the at least two ink cartridges are controlled by the pneumatic pump with pneumatic delivery ducts, branch ducts and a system that selects/diverts the compressed air flow and that is operatively connected between the pneumatic delivery ducts and branch ducts, and wherein the pneumatic delivery ducts are provided with check valves.

16 Claims, 13 Drawing Sheets

TATTOO MACHINE INK DISPENSER RESERVOIR STRUCTURE

DETAILED DESCRIPTION

Field of the Art

The tattoo machine is an electrical device handled by the tattoo artist for tendentially permanent decoration of the human body by introducing pigments under the epidermis into the dermis.

The prior art substantially reveals two types of functionally different tattoo machines and various aesthetically different machines:

a conventional type which uses a system of electromagnetic coils, defined and referred to as "coil machines" in order to determine a reciprocating linear motion with respect to a metal bar, at whose top part there are fixed one or more needles;

a relatively innovative type with a reciprocating electric motor, even with variable power by means of a potentiometer, defined and referred to as "rotary machine", which imparts a reciprocating motion to a fitting to which there can be interchangeably coupled heads or so-called needle-holder cartridges; the interchangeability thereof allowing to change the setting and use for different functions, for example both for outlining and colouring the conceived drawing, without necessarily requiring two machines.

Though less common, there are embodiments that are based on the two main types, on the one hand coil machines paired with needle-holder cartridges or interchangeable heads; on the other hand, rotary machines which actuate conventional bars carrying the needles at the top part.

In any case, in their alternating motion the needles fixed to the machine, irrespective of the type, penetrate into the skin leaving the pigments in the dermis, in the layer beneath the epidermis and not subject to continuous tissue replacement, which could cause the deterioration of the tattoo within a short period of time.

Irrespective of the mechanical instrument used, the tattoo artist continuously needs to dip the needle into the ink to carry out the required drawing.

The most common technique of tattoo artists in this regard is very empirical, they place ink trays on a surface, usually a translatable and orientable shelf within reach, into which they dip the needle continuously.

Forcing continuous ink pick-up movements by the operator, this technique is intuitively uncomfortable and dispersive; especially when the operator has to work on parts of the body that do not allow him/her to stay at a comfortable position, for example as concerns tattoos to be drawn on the back of persons laying down.

According to the prior art, there are some devices for supplying ink to the needle without having to dip it into the ink, for example international patent application publication number WO2017/131337A1, European patent application publication number EP2206530A1 and international patent application publication number WO2014/086342A2.

The present applicant devised a device, in various embodiments, suitable to associate ink reservoirs with tattoo machines, object of Italian patent no. 102018000007613.

Furthermore, these devices are basically not very practical for the operator when it comes to handling and they do not allow to mic the ink with diluent and adjust the mixing while carrying out the task.

OBJECTS OF THE INVENTION

In this context, the main object of the present invention is to provide an innovative and functional solution concept suitable to allow tattoo artists to carry out their tasks without having to continuously move to pick up the ink and at the same time to be able to dilute the ink and adjust the dilution thereof at will.

Another object of the present invention is to achieve the aforementioned objective through a solution suitable to adapt to existing tattoo machines, irrespective of the type, as well as suitable to be incorporated in machines contingently designed to use it.

Another object of the present invention is to achieve the preceding objects through a solution concept that is simple and efficient to implement, safe in use and cost-effective considering the results practically attainable therewith.

SUMMARY OF THE SOLUTION CONCEPT

These and other objects are all achieved by the tattoo machine ink dispenser reservoir structure, according to the present invention, which comprises: a handle in which at least two seats are made to house and retain at least two ink cartridges each being provided with occluding means pierced or suitable to be pierced for the introduction of air in use; a skin needle connected with the handle; connecting means to connect the at least two ink cartridges with the skin needle, wherein the connecting means comprises at least two nozzles; and a pneumatic pump, wherein the at least two ink cartridges are controlled by bt said pneumatic pump by means of pneumatic delivery ducts, branch ducts and means for the selecting/diverting the compressed air flow, wherein said means are operatively connected between the pneumatic delivery ducts and branch ducts, wherein the pneumatic delivery ducts are provided with check valves.

Further technical features of the tattoo machine ink dispenser reservoir structure, according to the present invention, are specified in the dependent claims.

DESCRIPTION OF THE ATTACHED DRAWINGS

Further characteristics and advantages of the tattoo machine ink dispenser reservoir structure according to the present invention shall be more apparent from the following detailed description of three relative preferred but non-exclusive embodiments, represented—solely by way of non-limiting example—in the thirteen attached drawings, wherein.

Figure 7:
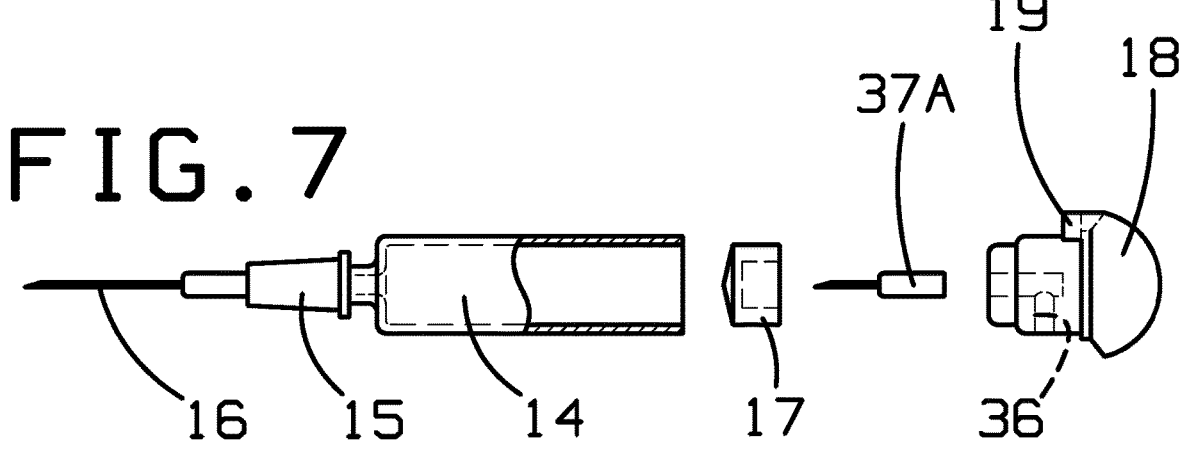
Figure 8:
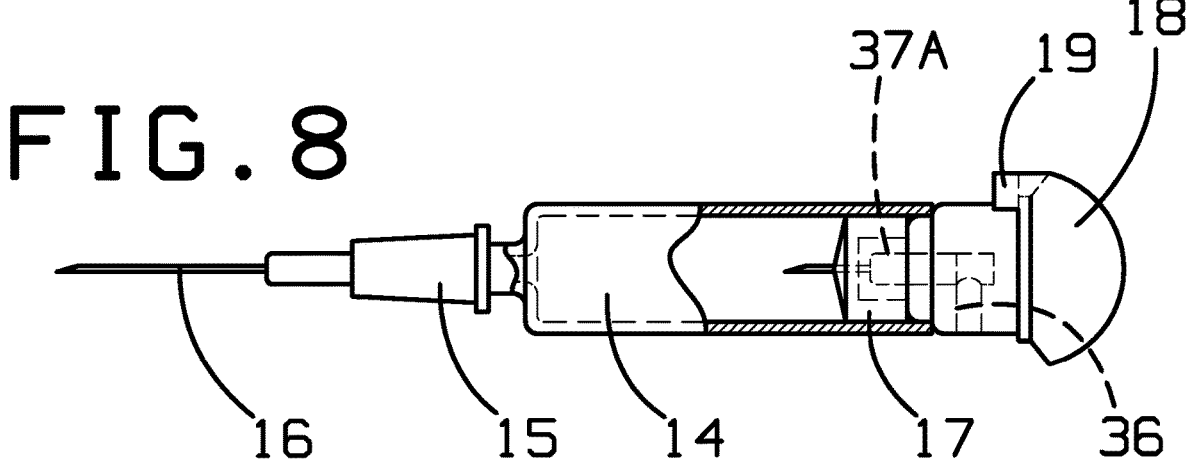
Figure 9:
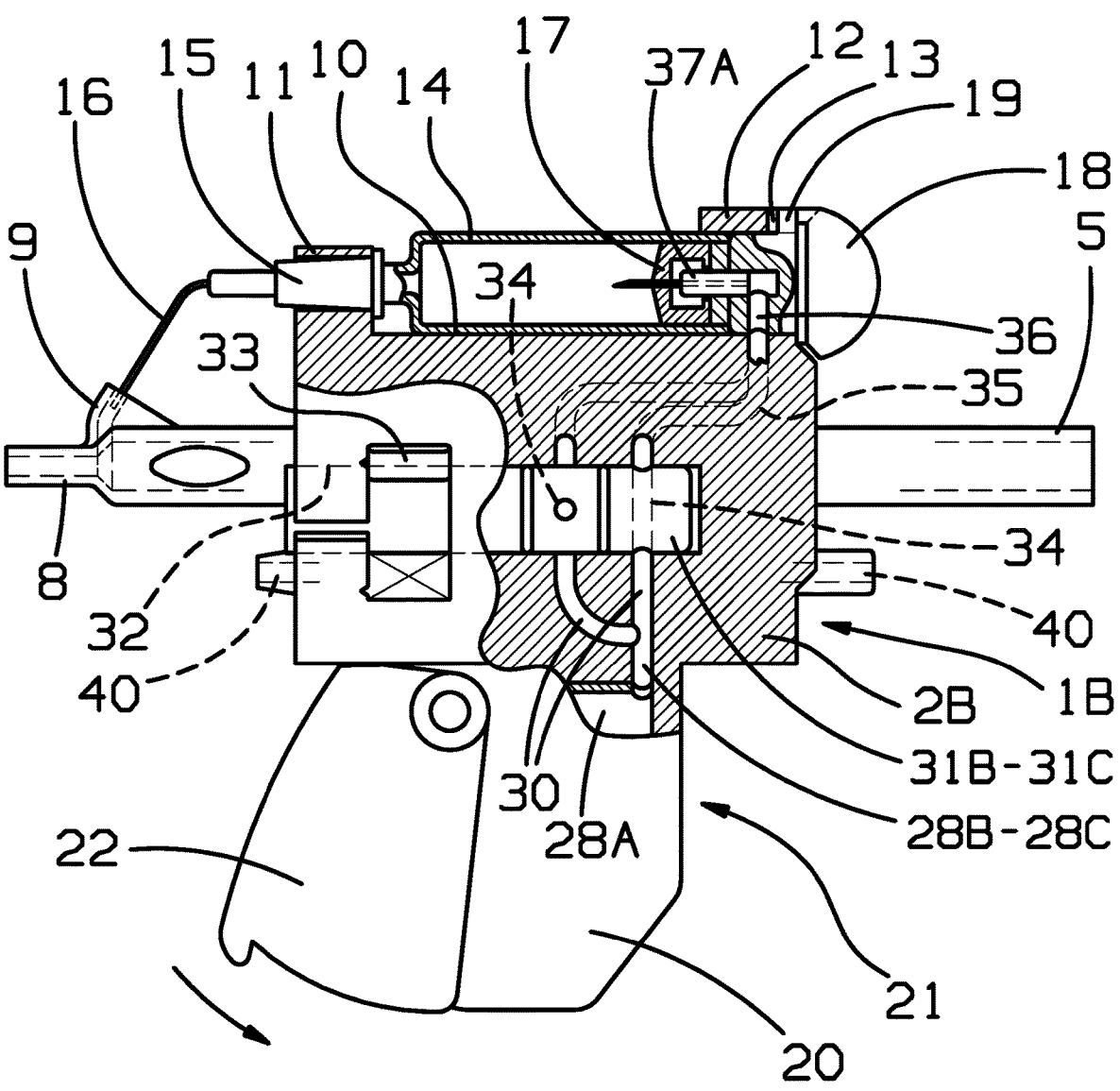
Figure 10:
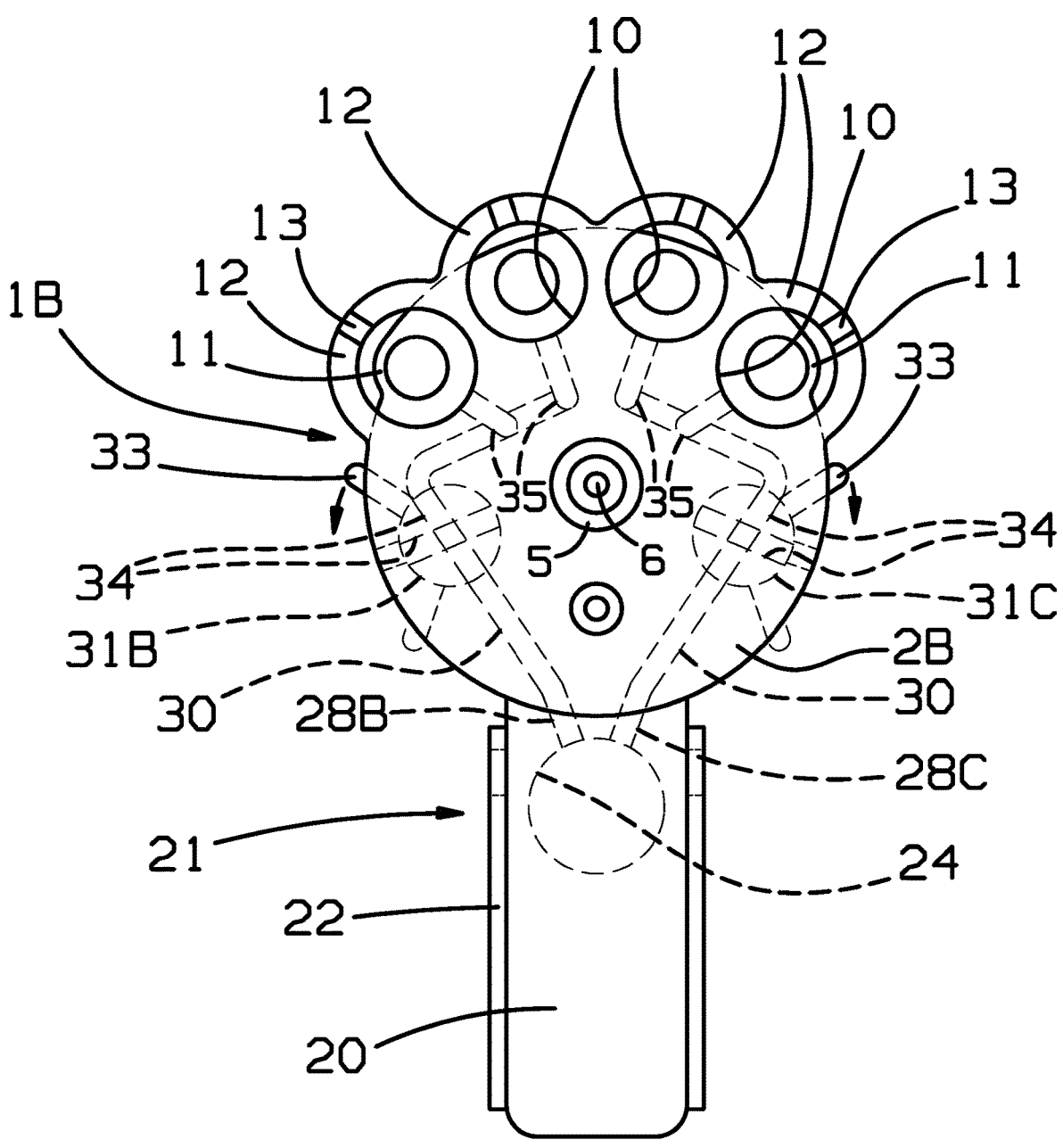
Figure 11:
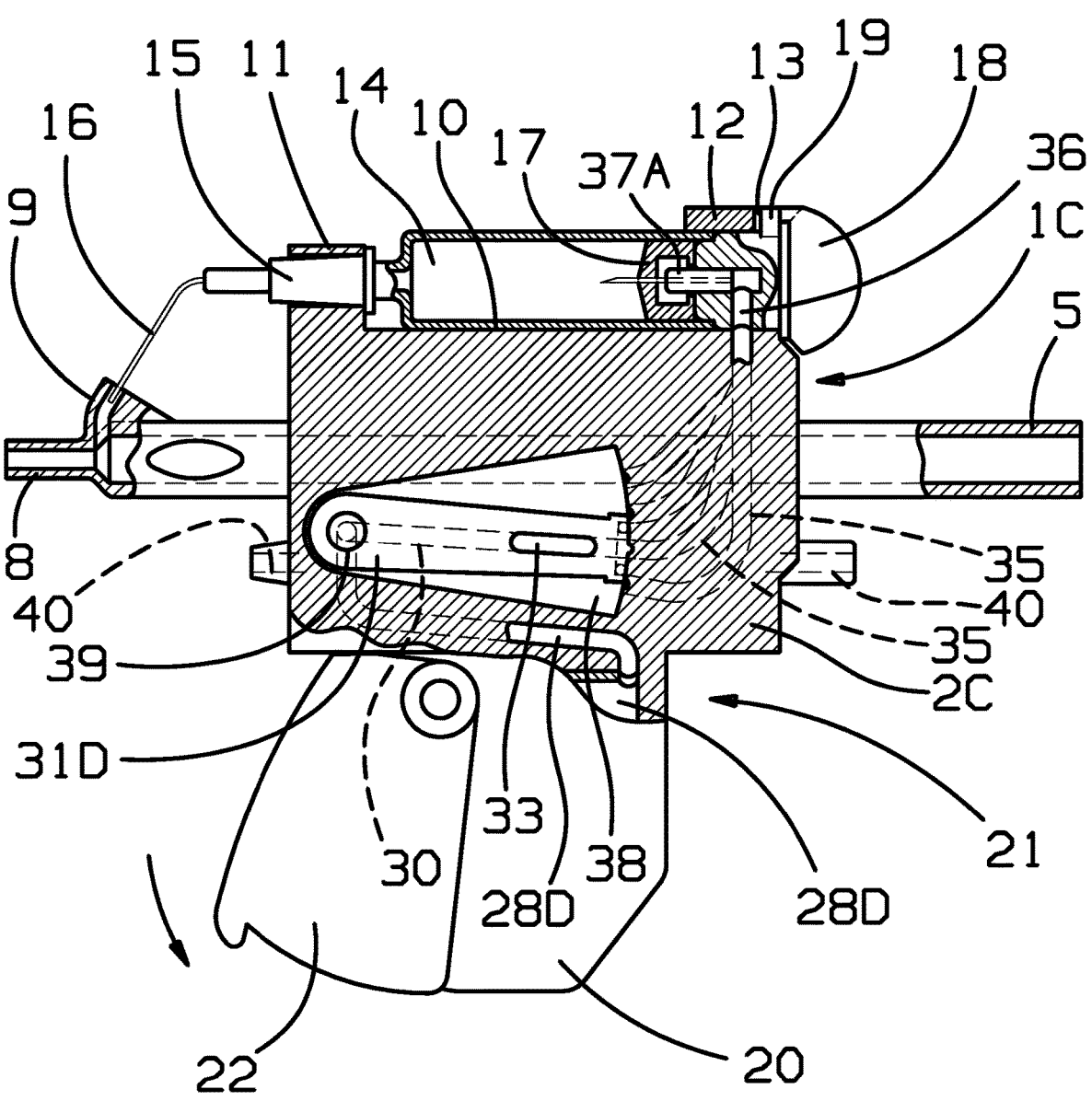
Figure 12:
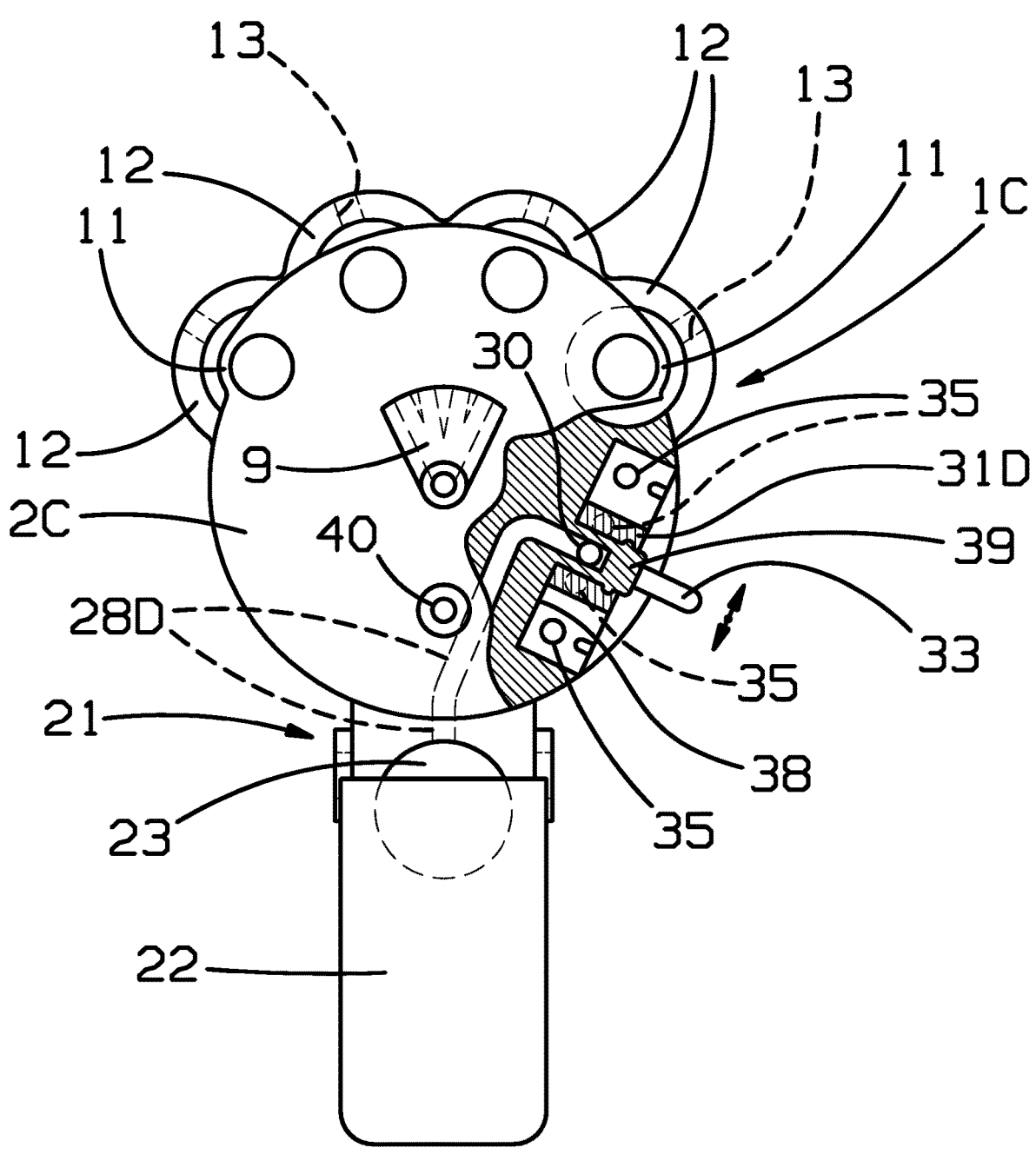
Figures 13, 14:
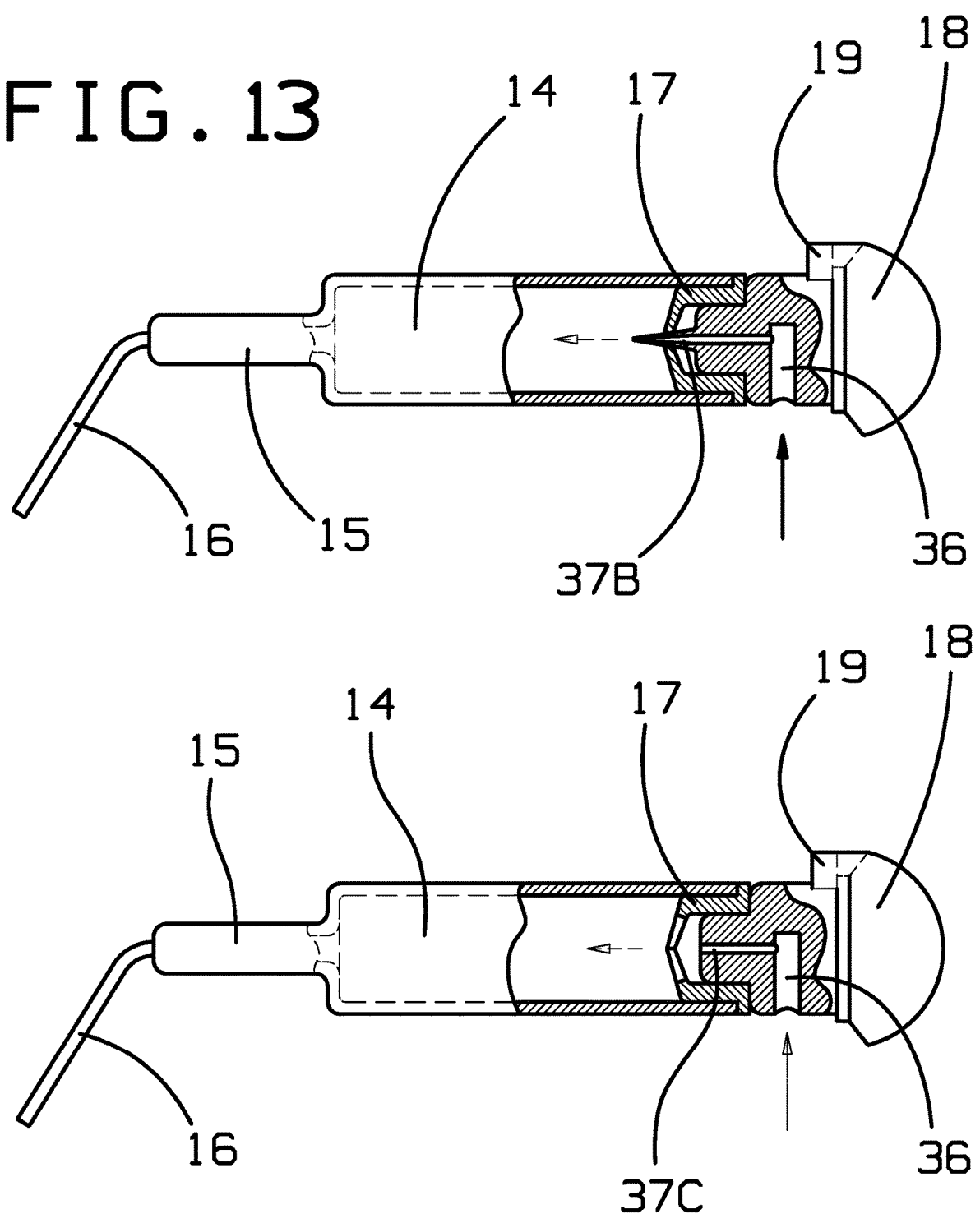
Figure 15:
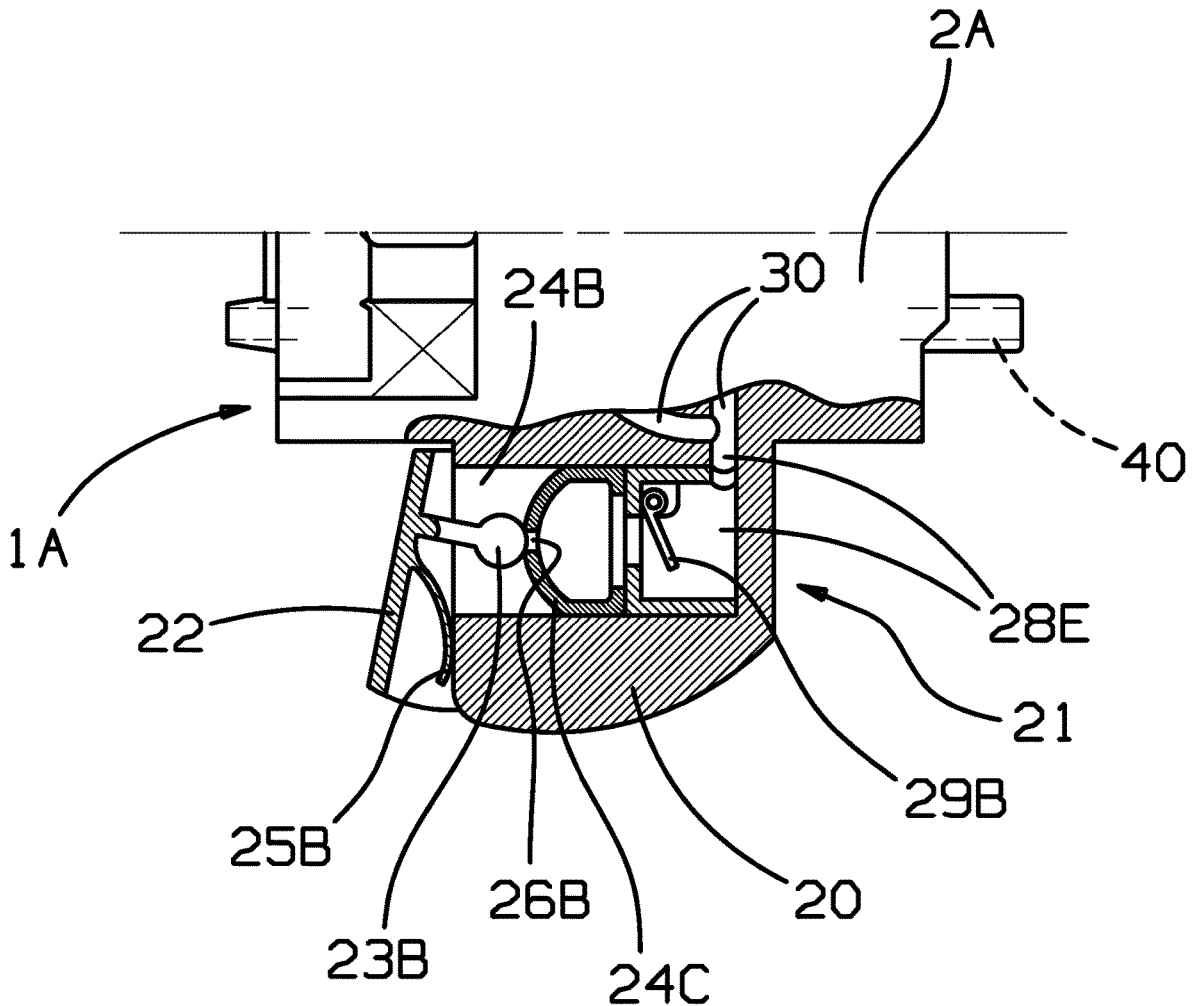

FIGS. 3 to 6 comprised are four rear cross-sectional views of a first embodiment of the tattoo machine ink dispenser reservoir structure according to the present invention in as many operating positions of the relative components FIGS. 7 and 8 show a lateral cross-section of a component element of the tattoo machine ink dispenser reservoir structure according to the present invention in an exploded and assembled view, respectively;

FIGS. 9 and 10 respectively show a lateral and rear cross-section of a second embodiment of the tattoo machine ink dispenser reservoir structure according to the present invention;

FIGS. 11 and 12 respectively show a lateral and front cross-section of third embodiment of the tattoo machine ink dispenser reservoir structure according to the present invention;

FIGS. 13 and 14 show a lateral cross-section of two alternative embodiments of a component element of the tattoo machine ink dispenser reservoir structure according to the present invention;

FIG. 15 shows a lateral cross-sectional view of a simplified alternative embodiment of a component element of the tattoo machine ink dispenser reservoir structure according to the present invention.

STATIC DESCRIPTION OF THE EMBODIMENT

Figure 1:
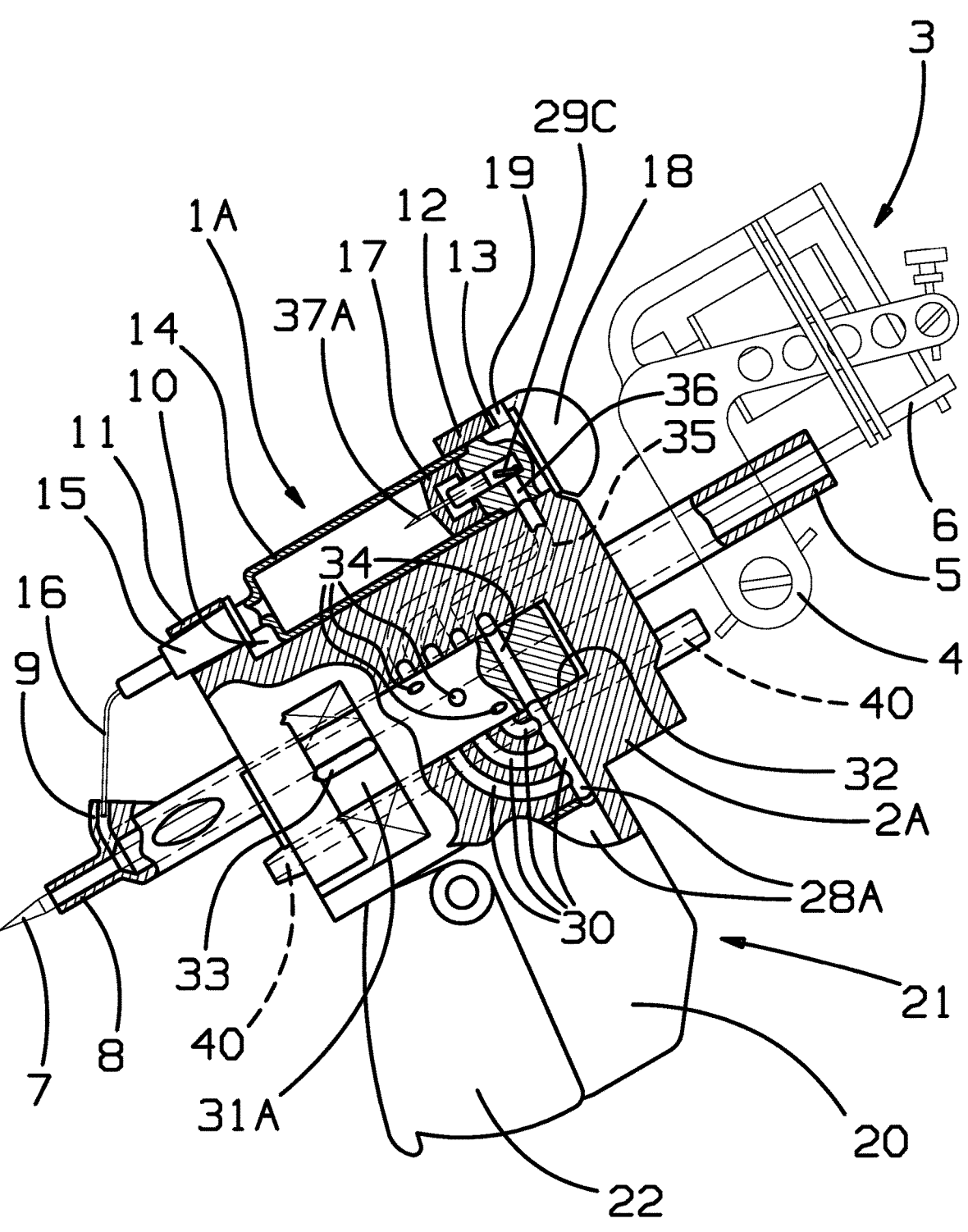
FIG. 1 is a lateral cross-section of a first embodiment of the tattoo machine ink dispenser reservoir structure according to the present invention as associated with a motor drive of a tattoo machine of the coil type according to the prior art.
Figures 1A, 2:
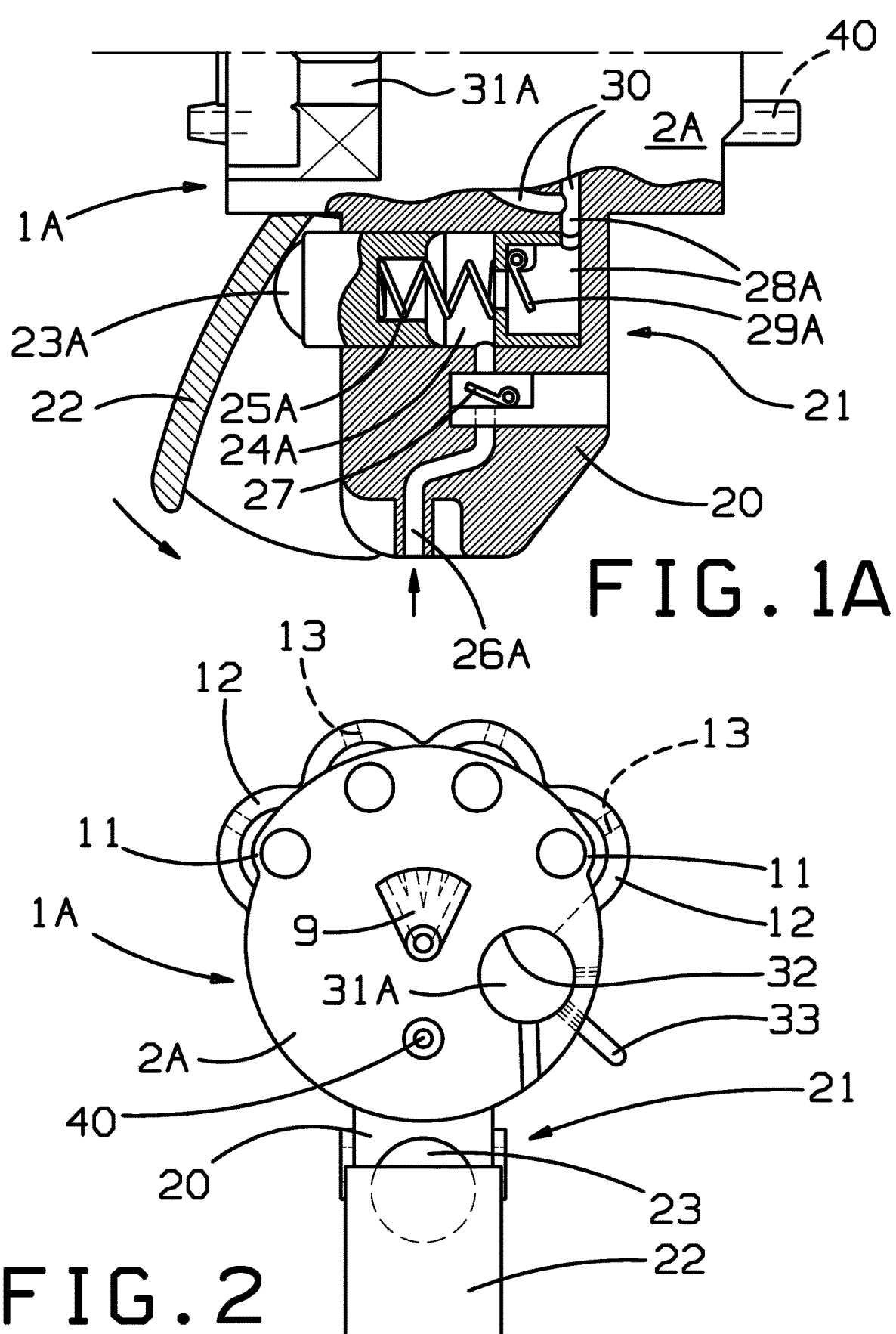
FIG. 1A is the cross-section of a detail of FIG. 1.
FIG. 2 is a front view of a first embodiment of the tattoo machine ink dispenser reservoir structure according to the present invention.
Figure 3:
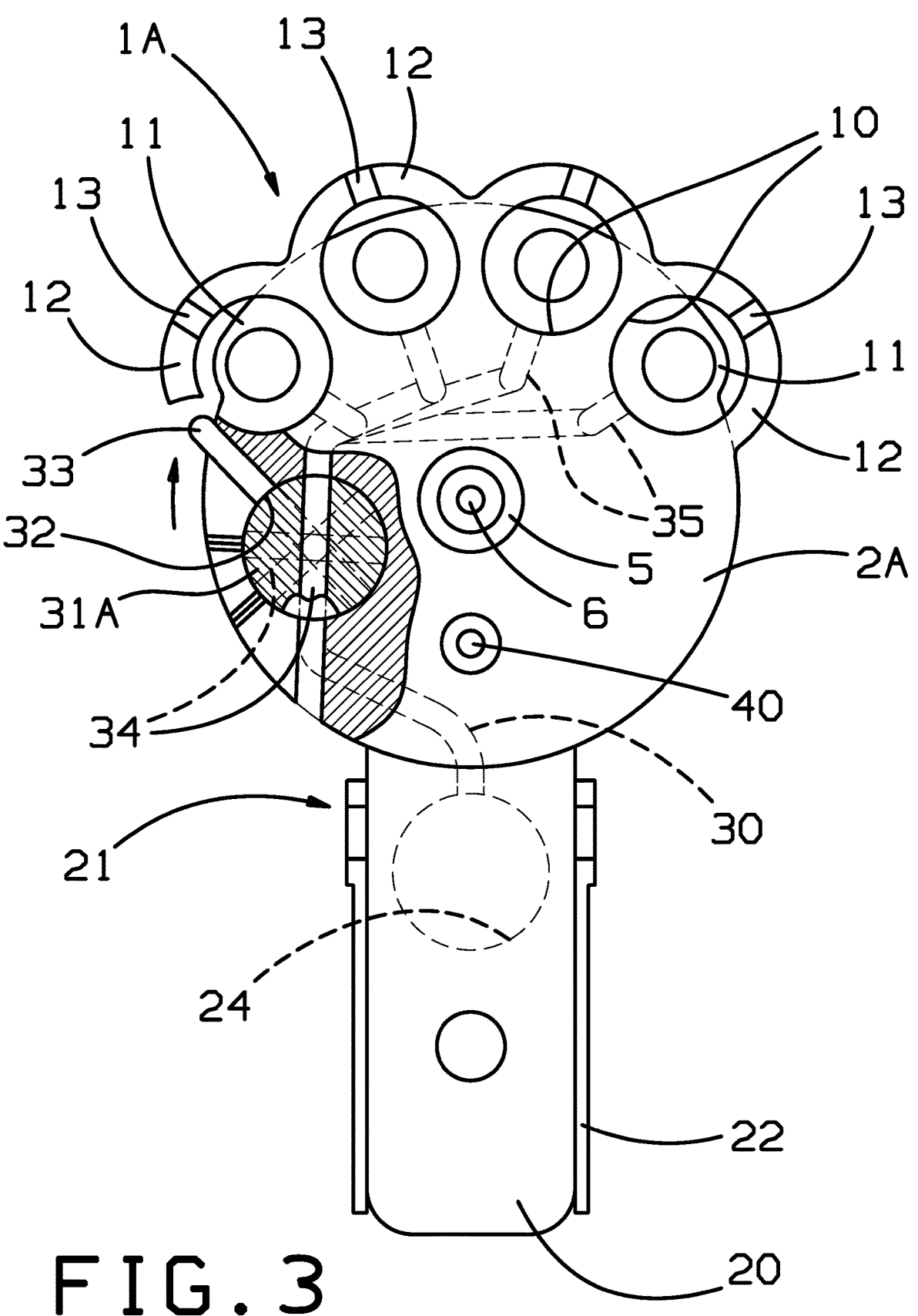
Figure 4:
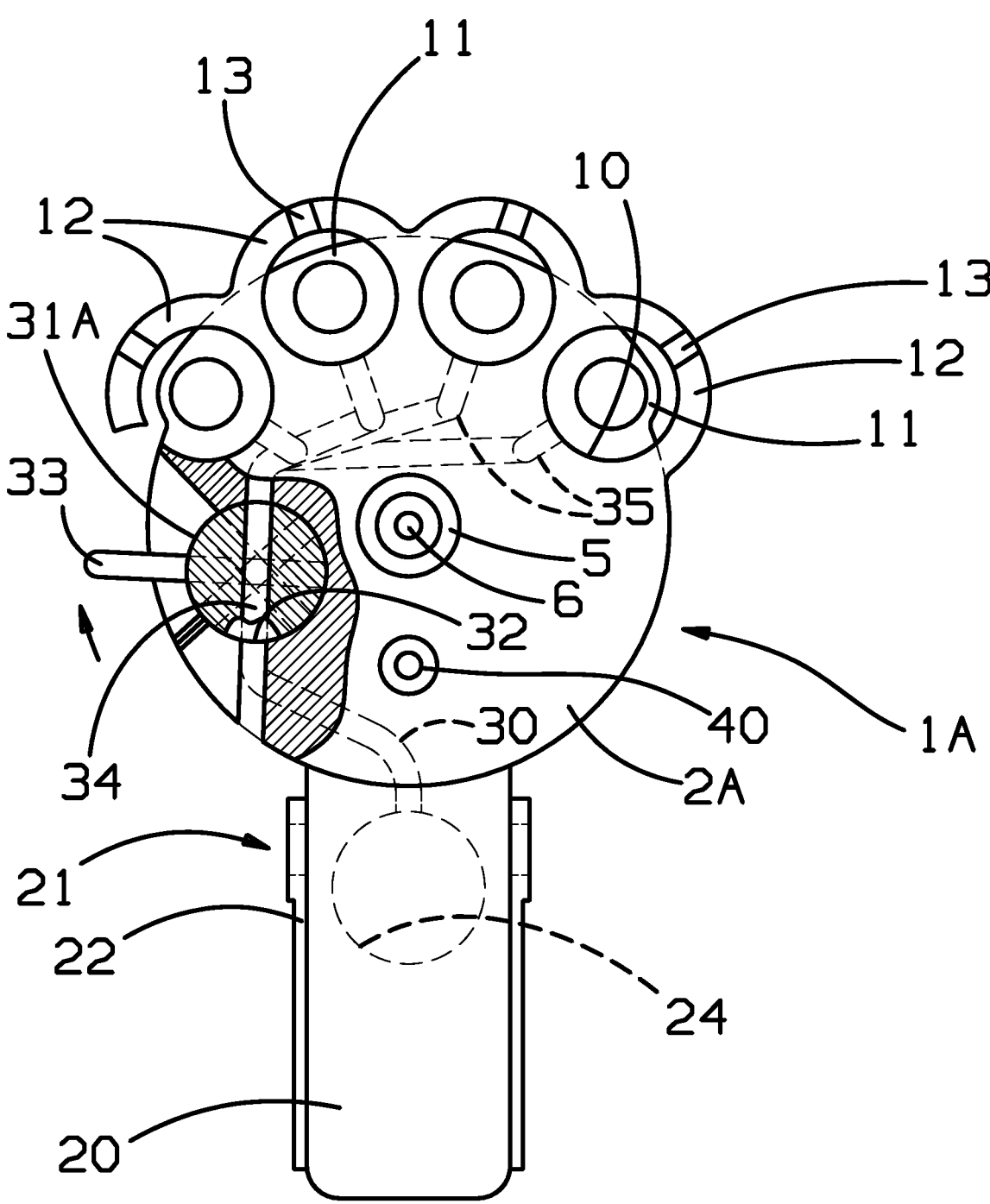
Figure 5:
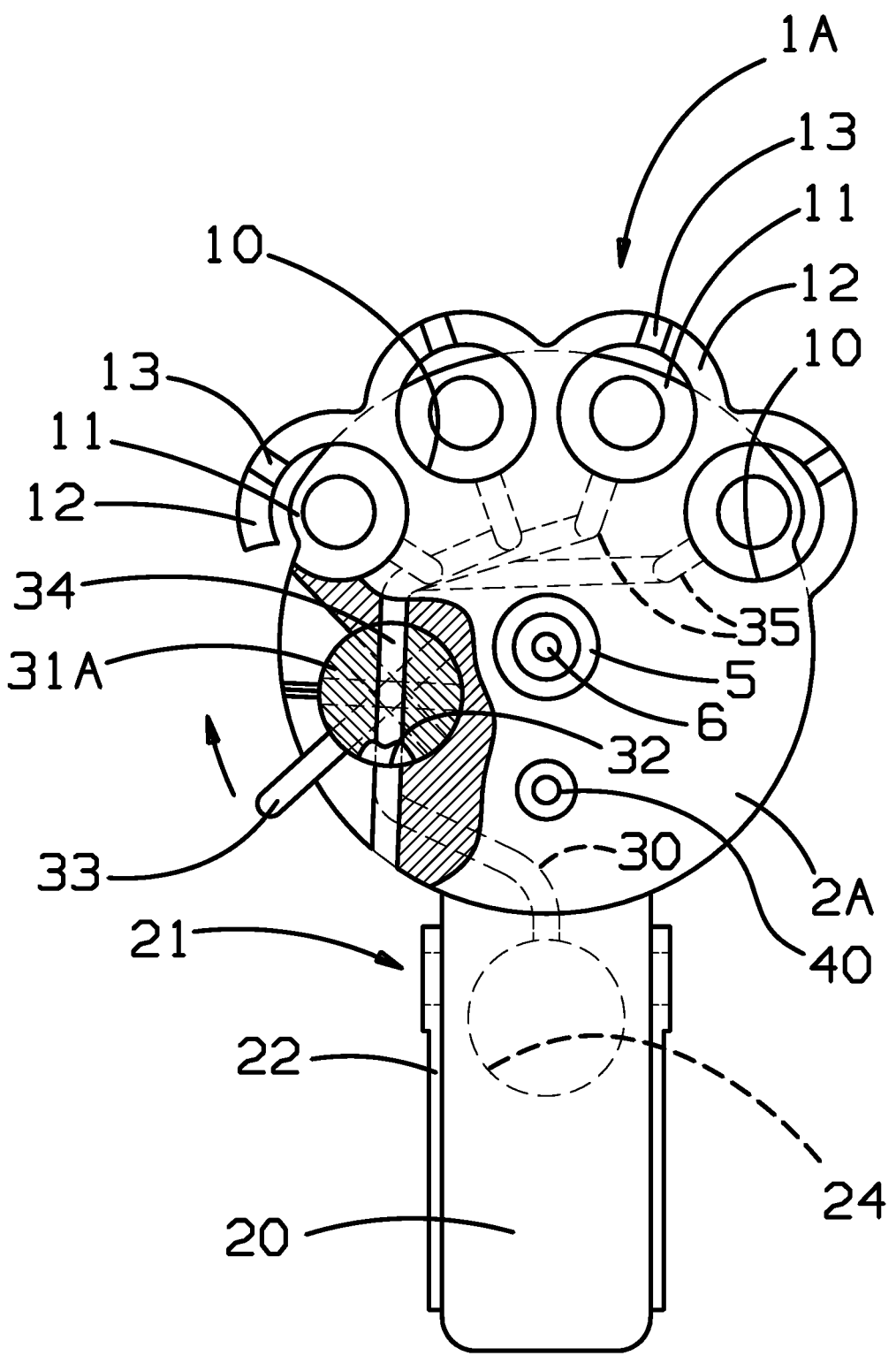
Figure 6:
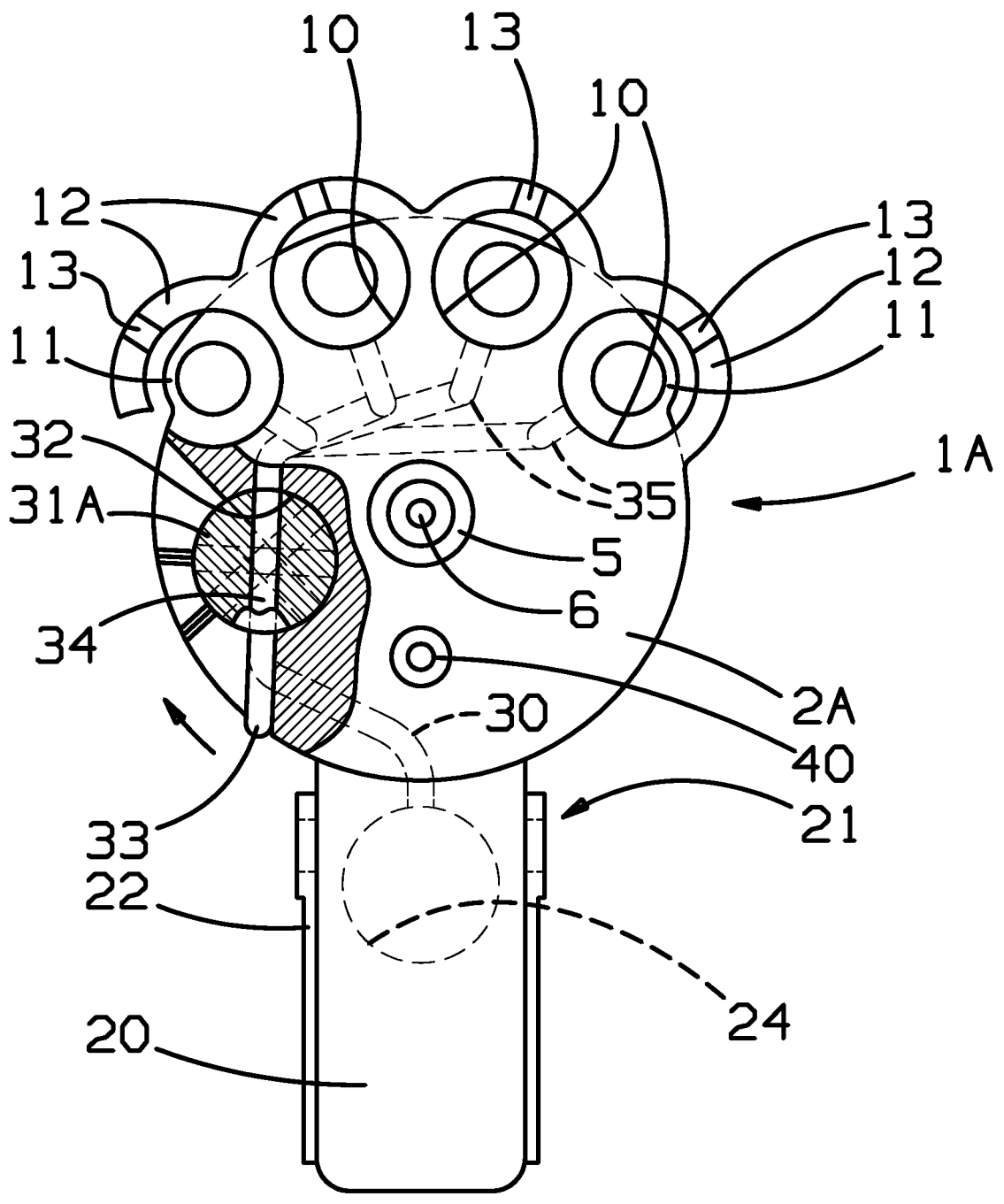

With reference to the figures and in particular to FIG. 1, a first embodiment of the tattoo machine ink dispenser reservoir structure according to the present invention, in this case applied to a coil-type machine, with motor drive, indicated in its entirety with 3, separated from the handle 2A, to which it is constrained by means of a clamp 4 which embraces an axial through pin 5 into which the axis 6 for moving the skin needle 7 is inserted, is shown with 1A.

The handle 2A is cylindrical and integrally joined with the axial pin 5 of the axis 6 for moving the skin needle 7, which protrudes from a tip 8 transversely provided with a funnel 9 which terminates close to the skin needle 7.

The cylindrical handle 2A a drum 2A, on whose jacket there are grooved four seats or cradles 10, having an arched cross-section and respective axes parallel to each other and according to the axis 6 for the reciprocating movement of the skin needle 7; the four seats or cradles 10 are arranged mutually on the upper section of the handle 2A, with reference to the gripping orientation for use as will be more apparent hereinafter.

Each seat 10 is provided, with reference to the orientation of the skin needle 7, of a distal tip stop element 11 and of a proximal retention arc 12, provided with a notch 13 on the outer keystone.

Retained in the seats 10 are respective interchangeable tubular cartridges 14, installed parallel to the axis of the skin needle 7, for containing the tattoo ink/dye.

The tubular cartridges 14 are distally provided with respective nozzles 15, retained within the tip stop element 11 of the cradles 10, at whose top part there depart deformable needles 16, suitable to be and remain bent to converge inside the funnel 9 of the tip 8 from which the skin needle 7 protrudes.

Alternatively, the needles 16 may be associated fixed to the tip stop element 11 and the tubular cartridges 14 may not be provided with them.

Filled with ink, the tubular cartridges 14 are proximally retained by the arc 12 and occluded by a hollow rubber 17, circumferentially abutting or not abutting against the thickness of the mouth of the cartridge 14, depending on the embodiments described below, and blocked by a shutter 18, which fits thereinto by penetrating the cartridge 14 and the proximal retention arc 12, taking an orientation with a tooth 19 which intercepts the notch 13 on the keystone of the proximal arc 12.

The handle 2A expands into a lower appendage 20, with reference to the gripping orientation for use as will be more apparent hereinafter and opposite to the groove section of the four seats or cradles 10 of the tubular cartridges 14; a trigger 22 is pivoted to said lower appendage 20.

Obtained in the lower appendage 20 is a pneumatic pump, indicated in its entirety with 21, consisting of a rounded head plunger 23A, which interacts with the trigger 22 and is slidably housed in a cylinder 24A, together with a counter spring 25A.

The cylinder 24 of the pump 21 is connected to the outside by means of a suction duct 26A, controlled by a suction check valve 27.

Furthermore, departing from the cylinder 24 of the pump 21 is a primary delivery duct 28A, having a circular cross-section just like all the ducts mentioned above and below, controlled by a delivery check valve 29A.

The primary delivery duct 28A, in the first alternative described below, branches into four delivery ducts 30, which terminate in line against a rotary pin selector 31A, in the relative seat 32 formed in the cylindrical handle 2A, provided with a radial grip slider 33 projecting outwards on one side of the cylindrical handle 2A, with reference to the gripping orientation for use as will be more apparent hereinafter.

Through the four deviator tunnels 34, respectively angled with respect to each other by 45° and mutually spaced by an amount equal to the interspace between the outlets of the four delivery ducts 30, diametrically pass through the selector pin 31A.

The mouths of the four branching ducts 35, which respectively terminate in the four shutters 18 of the tubular cartridges 14 lying and retained in the cradles 10 thereof, depart aligned on the wall of the seat 32 in a line diametrically opposite thereto.

Each of the shutters 18 houses its own branching duct 35 within a respective internal elbow-shaped connection duct 36 provided with a check valve 29C, each branching duct 35, by means of an external protrusion 37 thereof, leads into the rubber compartment 17 with which the respective shutter 18 is interfaced.

In the various embodiments, the external protrusion 37 of the shutters 18 can take the shape of a needle 37A, or of a spout 37B, or even a simple truncated pipe 37C (see FIGS. 7, 8, 13 and 14).

FIGS. 9 and 10 show a second embodiment 1B of the tattoo machine ink dispenser reservoir structure according to the present invention, wherein departing from the pump 21 are two delivery ducts 28B and 28C which are respectively split into a pair 30 with two rotary pin selectors 31B and 31C, with respective juxtaposed radial actuating sliders 33, and each reciprocatingly supply, through branching ducts 35, two shutters 18 and relative tubular cartridges or syringes 14.

FIGS. 11 and 12 show a third embodiment 1C of the tattoo machine ink dispenser reservoir structure according to the present invention, wherein the selector consists of a diverter lever 31D, with a segment-like actuation grip 33, for angular translation on a flat seat 38 obtained on the surface of the cylindrical handle 2C, around a fulcrum 39.

Passing through the fulcrum 39 is the primary delivery duct 28D and 30, which—at the outlet—can be reciprocatingly arranged to converge with the mouths, facing in a row on the flat seat 38, of the branching ducts 35 leading to the shutters 18 through the angular rotation of the diverter lever 31D, around the fulcrum 39.

FIG. 15 shows a simplified alternative embodiment of pneumatic pump 21, wherein the trigger 22 has a tab-like counter spring 25B and a spherical head appendage 23B which penetrates into the cylinder 24B and shuts off a hole 26B of an elastic bladder 24C housed therein, on whose other front there departs the primary delivery duct 28E, controlled by a delivery check valve 29B.

In all the embodiments shown by way of example, there is shown a channel 40 passing through the cylindrical handle 2, parallel to the axial pin 5, for possible supply of cleaning liquid close to the needle 7, coming from a reservoir and through pumping means, separate and not shown, for the purposes outlined hereinafter.

Dynamic Description of the Embodiment

Thus, having completed the static description of three preferred embodiment of the tattoo machine ink dispenser reservoir structure according to the present invention, following is the dynamic description of the same, i.e. the relative operation.

the cylindrical handle 2 can be associated with any pre-existing tattoo machine of the coil type 3 according to the prior art, by inserting the movement axis 6 into the axial pin 5 and locking it with the clamp 4; by suitably sizing the axial hole, the cylindrical handle 2 can be easily associated with any tattoo machine according to the prior art, even of the pen type.

The cylindrical handle 2 can be loaded with the tubular cartridges 14 containing liquid tattoo inks of different colours, by inserting them into the respective seats or cradles 10, where they remain retained by the distal tip stop elements 11 and by the proximal arcs 12, as well as blocked by the shutters 18, which penetrate the rubber elements 17, piercing them with the needle-like 37A or spout-like appendages 37B, or by engaging them without piercing them with the truncated pipe 37C in the embodiment with rubber elements previously pierced (see FIGS. 7, 8, 13 and 14), as better outlined hereinafter.

At this point the cylindrical handle 2 is ready to be gripped by the tattoo artist between thumb, forefinger and possibly medium finger like a usual tattoo machine handle, but with the appendix 20 projecting under the palm of the hand and the relative trigger 22 actuatable by the other fingers.

The pneumatic pump 21 can be actuated by actuating the trigger 22:

Housed inside the cylinder 24A together with the counter spring 25A, the plunger 23A is therefore moved in an active stroke in which the plunger 23A is pushed into the cylinder 24A to compress the spring 25A; while releasing the trigger 22 actuates a passive stroke in which the plunger 23A is pashed backwards; these two strokes of the plunger 23A inside and outside the cylinder 24A, represent the entire cycle of the pump 21:

during the active stroke, the plunger 23A constricts the volume of the cylinder 24A, forcing the air out of the pump 21 into the delivery ducts 28A and 30, which are opened—due to the pressure difference—by the delivery check valve 29A, whereas the suction check valve 27 is closed by the pressure difference on the contrary;

conversely, in the passive stroke when the trigger 22 is released, the spring 25A which pushes the plunger 23A backwards expands the volume of the cylinder 24A, suctioning air from the outside through the suction duct 26A, which is opened due to pressure difference—by the suction check valve 27, while the delivery check valve 29A is closed by the pressure difference.

In the simplified embodiment of the pump 21 shown in FIG. 15, the same end is achieved by actuating the trigger 22, which moves the spherical head appendage 23B inside the cylinder 24B to occlude the hole 26B of the elastic bladder 24C and to compress it against the elasticity thereof to forcibly eject the air contained within the delivery ducts 28E and 30, opened—due to pressure difference—by the delivery check valve 29B;

upon release, the trigger 22 is pushed back by the elasticity of the tab 25B, releasing the fork 26B of the bladder 24C which, by its own elasticity, expands again, drawing air through the fork 26B itself thus opened for a new cycle of the pump 21.

The pressurised air flows thus introduced into the primary delivery ducts 28 and 30 can be managed by the tattoo artist, directing them reciprocatingly toward the cartridge 14 containing the ink to be duly used.

Management occurs by means of the selectors 31:

in the example of a single rotary cylindrical selector 31A, the tattoo artist has the radial grip slider 33 substantially within the reach of the thumb and by rotating it—without the need to interrupt his/her drawing and/or colouring work, possibly and preferably assisted in positioning by a simple reliefs or notches snap-acting mechanism—he/she connects one and exclusively one delivery duct 30 to one and exclusively one branching duct 35, actuating a connection exchange by shutting off the branching duct 35 with the delivery duct 30 by means of a fitting of a pre-selected deviator tunnel 34 of the selector 31A, while the body of the selector pin 31A occludes all the other ducts 30 and 35.

The flow, or rate, of pressurised air thus directed reaches the pre-selected cartridge 14 by means of the angular connection 36 of the respective shutter 18 and relative external protrusion 37, for example the needle 37A which pierced the membrane of the hollow rubber 17 during the functional positioning of the cartridge 14, and it creates a pressure—within the cartridge 14—which forces a drop of ink to flow out through the needle 16 and drop back into the funnel 9 of the tip 8 up to the skin needle 7 to actuate the desired colouring of the drawing being carried out.

The backflow of the ink once the pressure on the duct—where it tends to occur—ceases is inhibited by the anti-backflow valve 29C of the shutters 18 which prevents the ink from returning to the duct should it not already find sufficient resistance against backflow.

In the embodiment with duplication of the rotary pin selectors 31B and 31C, it operates in the same manner, but the tattoo artist has two juxtaposed radial sliders 33 available, one to be actuated with the thumb and the other with the index finger, to select the air flow path and obtain the desired ink drop on the skin needle 7.

In the third embodiment, the tattoo artist has within a thumb's reach a lever 31D, this also preferably assisted in positioning by a reliefs or notches snap-acting mechanism, to channel the air flow into the branching duct 35 suitable to reach the desired cartridge appliance 14, without prejudice to the other operation characteristics.

FIGS. 7, 8, 13 and 14 show the various ways in which the cartridge 14 can be penetrated by the air flow:

with regard to FIGS. 7 and 8, shown therein in detail is the alternative embodiment with shutter 18 provided with needle-like protrusions 37A for piercing the rubber element 17 described so far;

FIG. 13 shows an alternative in which the rubber element 17 circumferentially abuts against the thickness of the cartridge 14 and the shutter 18 is provided with spout-like protrusions 37B for piercing the rubber element 17;

FIG. 14 shows an alternative in which the rubber element 17 circumferentially abuts against the thickness of the cartridge 14 and it is already pierced and the shutter 18 is provided with truncated pipe protrusions 37 to provide the air jet which the membrane of the rubber element 17, previously pierced and specifically provided with a valve hole—as mentioned—allows to pass through due to the elasticity thereof, deforming and swelling under the pressure of the jet and thus widening the hole which substantially tends to close to block the backflow once the pressure ceases.

In this context, it should be observed that the operation of the cartridges 14 may be alternatively, even if not preferably, conceived as that of an actual syringe, that with the rubber element 17, suitably sized, stabilised and materialised for this purpose, operating as an actual plunger, slidable inside the cartridge 14, which—in this embodiment—substantially becomes a syringe 14, as a result of the pressure of the air behind it, which does not pass through it in this embodiment (not shown).

The through duct 40 is in any case an optional accessory but useful for directing a detergent liquid flow onto the treated epidermis, supplied by means of an appropriate method, see for example patent IT102018000001927.

Alternative Embodiments

It is obvious that in further alternative embodiments still falling within the innovation concept subject of the embodiment illustrated above and claimed below, the tattoo machine ink dispenser reservoir structure according to the present invention, may be implemented through equivalent technical and mechanical solutions, i.e. provided with further supplementary solutions, just like—in the claimed scope—all elements they are made of may vary in a manner suitable for the purpose and adapted to the specific conformation and structure.

In particular:

the tattoo machine ink dispenser reservoir structure according to the present invention may also be applied to reciprocating electric motor machines; adapting the axial hole of the drum in the case of machines with a single pen-shaped body.

Besides the three examples of selectors shown in the three embodiments, selectors of any kind and type suitable for the purpose of channelling the compressed air flows coming from the pneumatic pump into one or the other of the ducts to reach various cartridges or syringes may be alternatively conceived.

In the three shown embodiments, the ducts are all obtained from the solid portion of the drum, but alternatively they may be also obtained from external cannulas suitably connected to the apices.

The pneumatic pump, if necessary, may be provided with check valves which prevent the backflow of the ink, for example consisting—in a known manner—of a ball which is arranged to occlude a hole and retained therein by a counter spring so as to block the flow of the fluid when it is not pressed; or any other type of check valve embedding a slider.

Advantages of the Invention

As observable from the preceding detailed description of three preferred embodiments, the tattoo machine ink dispenser reservoir structure according to the present invention offers an advantage corresponding to the attainment of these and other pre-set objects:

as a matter fact, it allows to attain a relatively simple, modular and polyvalent solution for appropriately adjusting ink doses in the tattoo needle without the need for dipping it and with the possibility of changing the ink during the operation without interruptions.

Furthermore, the solution can be interchangeably adapted to substantially all the tattoo machines existing on the market, without conversely, requiring any adaptation of the latter.

KEY TO REFERENCE NUMBERS

1A) first embodiment of the ink dispenser reservoir
1B) second embodiment of the ink dispenser reservoir
1C) third embodiment of the ink dispenser reservoir
2A) cylindrical handle in the first embodiment
2B) cylindrical handle in the second embodiment
2C) cylindrical handle in the third embodiment
3) motor drive
4) clamp
5) axial pin
6) movement axis
7) skin needle
8) tip
9) tip funnel
10) seats or cradles of cartridges or syringes
11) tip stop element of the distal retention seats or cradles of cartridges or syringes
12) proximal arc of the retention seats or cradles of the cartridges or syringes
13) proximal arc notch of the seats or cradles of cartridges or syringes
14) tubular cartridges or syringes
15) nozzles of tubular cartridges or syringes
16) deformable needles of tubular cartridges or syringes
17) hollow rubber elements for tubular cartridges or syringes
18) shutters of tubular cartridges or syringes
19) tooth of shutters interacting with the proximal arc notch of the seats or cradles of cartridges or syringes
20) lower appendage of the drum handle
21) pneumatic pump in its entirety
22) pump trigger
23A) pump plunger
23B) spherical head appendage of the trigger in the simplified embodiment
24A) pump cylinder
24B) pump cylinder in the simplified embodiment of the pump
24C) elastic bladder in the simplified embodiment of the pump
25A) counter spring of the pump
25B) spring of the tab-like trigger in the simplified embodiment of the pump
26A) suction duct
26B) hole of the elastic bladder in the simplified embodiment of the pump
27) suction check valve
28A) primary delivery duct in the first embodiment
28B) primary delivery duct in the second embodiment
28C) primary delivery duct in the second embodiment
28D) primary delivery duct in the third embodiment
28E) primary delivery duct in the simplified pump embodiment
29A) delivery check valve
29B) delivery check valve in the simplified embodiment of the pump 29C) anti-backflow valve of the shutters 30) branching ducts of the primary delivery duct 31A) rotary pin selector in the first embodiment 31B) rotary pin selector in the second embodiment 31C) rotary pin selector in the second embodiment 31D) diverter lever selector in the third embodiment 32) seats of the rotary pin selector 33) radial grip slider of the rotary pin selectors 34) deviator tunnels diametrically passing through the rotary pin selectors 35) branching ducts 36) elbow-shaped connection ducts for the shutters 37) external protrusions of the elbow-like channels 37A) needle-shaped conformation of the external protrusion of the elbow-like channels 37B) spout-like conformation of the external protrusion of the elbow-like channels 37C) truncated pipe shaped conformation of the external protrusion of the elbow-like channels 38) flat seat of the diverter lever on the cylindrical handle in the third embodiment 39) fulcrum of the diverter lever 40) through channel for supplying the cleaning liquid

The invention claimed is:

1. A tattoo machine ink dispenser reservoir structure, comprising:
 a handle (2), in which at least two seats (10) are defined to house and retain at least two ink cartridges (14) each provided with occluding means (17) pierced or adapted to be pierced for introduction of air when in use;
 a skin needle (7) connected to the handle (2);
 connecting means (15, 16, 9) to connect the at least two ink cartridges (14) with the skin needle (7), wherein the connecting means (15, 16, 9) comprise at least two nozzles (15) and
 a pneumatic pump (21), wherein the at least two ink cartridges (14) are controlled by said pneumatic pump (21) with pneumatic delivery ducts (28, 30), branching ducts (35) and selecting/diverting means (31) for a compressed air flow,
 wherein said selecting/diverting means (31) are operatively connected between the pneumatic delivery ducts (28, 30) and branching ducts (35), and
 wherein the pneumatic delivery ducts (28, 30) are provided with check valves (27, 29).

2. The tattoo machine ink dispenser reservoir structure according to claim 1, wherein the at least two ink cartridges are four parallel ink cartridges each comprising a cylindrical cannula, wherein in the handle (2) there are provided four cradle-shaped seats (10) shaped to house and retain the four parallel radial ink cartridges (14), and wherein said ink cartridges (14) are controlled by said pneumatic pump (21) of a manual trigger type (22) through the pneumatic delivery ducts (28, 30) and the branching ducts (35) intermediated by selecting/diverting means (31).

3. The tattoo machine ink dispenser reservoir structure according to claim 1, wherein said handle (2A) is substantially cylindrical, and wherein said at least two seats (10) have axes parallel to each other and to a rod (6) for a reciprocating movement of the skin needle (7) and arranged on an upper section of the handle (2A) with reference to an orientation of gripping when in use, and wherein said rod (6) is connected with said handle (2A).

4. The tattoo machine ink dispenser reservoir structure according to claim 1, wherein each of the at least two seats (10) is provided, with orientation reference to the skin needle (7), with a distal tip-lock (11).

5. The tattoo machine ink dispenser reservoir structure according to claim 1, wherein the at least two ink cartridges (14) are interchangeable.

6. The tattoo machine ink dispenser reservoir structure according to claim 1, wherein each of the at least two seats (10) is provided with a proximal retaining arc (12) provided with a notch (13) on an outer face, and wherein said occluding means (17) comprise a hollow rubber (17), circumferentially abutting or not abutting against a thickness of a mouth of a respective ink cartridge (14) and blocked by a shutter (18) which is engaged by penetrating the respective ink cartridge (14), the proximal arc (12) being oriented with a tooth (19) which intercepts the notch (13).

7. The tattoo machine ink dispenser reservoir structure according to claim 6, wherein said shutter (18) has an internal elbow-shaped connection duct (36), which by means way of an outer protrusion terminates into a cavity of the hollow rubber (17) to which elbow-shaped connection duct is interfaced.

8. The tattoo machine ink dispenser reservoir structure according to claim 7, wherein said outer protrusion (37) comprises a needle (37A), a spout (37B), or a truncated pipe (37C), and wherein said hollow rubber (17) is pierced by said outer protrusion (37) or is pierced beforehand.

9. The tattoo machine ink dispenser reservoir structure according to claim 6, wherein the shutter has a check valve (29C) against a backflow of a pigment.

10. The tattoo machine ink dispenser reservoir structure according to claim 6, wherein:
 a primary delivery duct (28D) passes through a fulcrum (39) of a deviator lever (3 ID) with a protruding actuation grip (33) for angular translation on a flat seat (38) formed on a surface of the handle (2C);
 an extension (30) of the primary delivery duct (28D) terminating on the flat seat (38) radially passes through a deviator lever (31D) branching from the fulcrum (39); and
 faced on a flat seat (38) in a row so as to be reciprocatingly shut off by an outlet of the extension (30) of the primary delivery duct (28D), there are inlets of the branching ducts (35), which respectively supply the four shutters (18) of the ink cartridges (14) lying and held in the seats (10) thereof.

11. The tattoo machine ink dispenser reservoir structure according to claim 1, wherein said occluding means (17) comprise a pneumatically displaced plunger.

12. The tattoo machine ink dispenser reservoir structure according to claim 1, wherein said pneumatic pump (21) comprises a piston (23 A) interacting with a trigger (22) and housed slidably inside a cylinder (24A) together with a counter spring (25 A) externally connected by a suction duct (26A) controlled by a check valve (27), from which there departs at least one of the delivery ducts (28A, 28B, 28C, 28D) controlled by a delivery check valve (29A).

13. The tattoo machine ink dispenser reservoir structure according to claim 1, wherein said pneumatic pump (21) is formed by an elastic bladder (24C) with a hole (26B) occluded by a stroke of a trigger (22).

14. The tattoo machine ink dispenser reservoir structure according to claim 13, wherein the trigger (22) has a tab-shaped counter spring (25B) and a spherical head appendage (23B) which penetrates into a compartment (24B) and shuts off a hole (26B) of an elastic bladder (24C) housed therein, on whose other front there departs a primary delivery duct (28E), controlled by a delivery check valve (29B).

15. The tattoo machine ink dispenser reservoir structure according to claim 1, wherein:

a primary delivery duct (28 A) branches into four delivery ducts (30), which terminate in line against a rotary pin selector (31A), in a respective seat (32) formed in the handle (2A) with a longitudinal extension parallel to a rod (6) for moving the skin needle (7), provided with a radial grip slider (33) projecting outwards on one side of the handle (2A), with reference to a gripping orientation when in use;

four deviator tunnels (34), respectively angled with respect to each other by 45° and mutually spaced by an amount equal to an interspace between outlets of the four delivery ducts (30), four deviator tunnels (34) passing through the selector pin (31A);

mouths of the four branching ducts (35), which respectively terminate in the four shutters (18) of the ink cartridges (14) lying and held in the seats (10) thereof, depart in line on a wall of the respective seat (32) in a line diametrically opposite thereto.

16. The tattoo machine ink dispenser reservoir structure according to claim 1, wherein:

two primary delivery ducts (28B, 28C) branch each into two secondary delivery ducts (30), respectively terminating in line against two rotary pin selectors (31B, 31C) in respective seats (32) made parallel in the handle (2B) with a longitudinal extension parallel to a rod (6) for moving the skin needle (7), the handle being provided with respective radial grip sliders (33) oppositely protruding outwards on two cylindrical griping sides (2B), with reference to a gripping orientation when in use;

two deviator tunnels (34), respectively angled with respect to each other by 90° and mutually spaced by an amount equal to an interspace between outlets of the two secondary delivery ducts (30), the two deviator tunnels passing through the two selector pins (31B, 31C); and mouths of the two branching ducts (35), which respectively terminate in four shutters (18) of the ink cartridges (14) lying and held in the seats (10) thereof, depart in line on respective walls of the respective seat (32) in a line diametrically opposite thereto.

\* \* \* \* \*